United States Patent [19]

Onitsuka et al.

[11] Patent Number: 4,557,830

[45] Date of Patent: Dec. 10, 1985

[54] PACKED COLUMN HAVING PRESSURE-ABSORBING MECHANISM

[75] Inventors: Hatsuki Onitsuka, Nobeoka; Shin Saito; Hideo Fukuda, both of Hyuga, all of Japan

[73] Assignee: Asahi Kasei Kogyo Kabushiki Kaisha, Osaka, Japan

[21] Appl. No.: 594,271

[22] Filed: Feb. 27, 1984

[30] Foreign Application Priority Data

Apr. 26, 1983 [JP] Japan .................................. 58-72268

[51] Int. Cl.$^4$ ............................................. B01D 15/08
[52] U.S. Cl. ................................... 210/198.2; 55/386; 210/286
[58] Field of Search ..................... 210/198.2, 279, 286; 55/386

[56] References Cited

U.S. PATENT DOCUMENTS

| | | | |
|---|---|---|---|
| 3,202,286 | 8/1965 | Smit | 210/286 |
| 3,230,167 | 1/1966 | Golay | 210/198.2 |
| 3,522,172 | 7/1970 | Pretorius et al. | 210/198.2 |
| 3,657,864 | 4/1972 | Davis et al. | 55/386 |
| 4,259,186 | 3/1981 | Boeing | 210/198.2 |
| 4,448,695 | 5/1984 | Gordon, Jr. et al. | 210/286 |

FOREIGN PATENT DOCUMENTS 1203439 8/1970 United Kingdom .

Primary Examiner—John Adee
Attorney, Agent, or Firm—Sprung Horn Kramer & Woods

[57] ABSTRACT

When a packed column having a pressure-absorbing mechanism satisfies the following conditions, the pressure absorbing mechanism has a sufficient packings-supporting ability in spite of its simplicity, the disorder of flow of fluid is slight and the effect of separation of materials is high: (1) the inside diameter (D cm) is 10 cm or more, (2) the aforesaid pressure-absorbing mechanism comprises solid parts and passage spaces through which packings can pass, (3) the specified circumference ratios of most of said passage spaces are 10/D or more and their lengths in the flow direction are larger than the −1.5th power of the circumference ratio, (4) the above passage spaces exist within 1 cm from any position on the upper and lower sides of the aforesaid solid parts, and (5) the specified shielding degree of the pressure-absorbing mechanism is 0.01 or more and 0.8 or less.

7 Claims, 48 Drawing Figures

FIG. 2
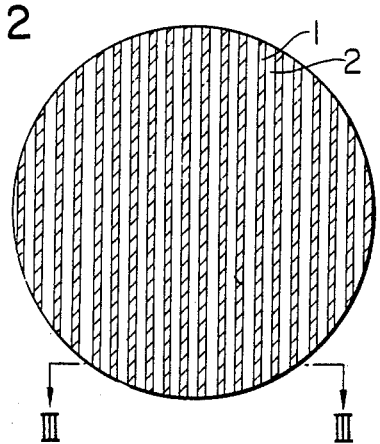
FIG. 3-(i)    FIG. 3-(ii)    FIG. 3-(iii)
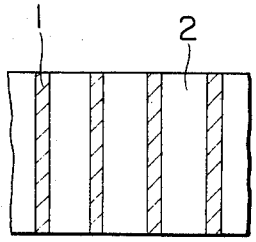 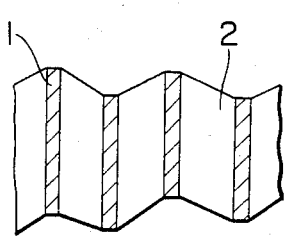 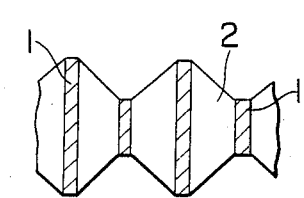
FIG. 3-(iv)    FIG. 3-(v)
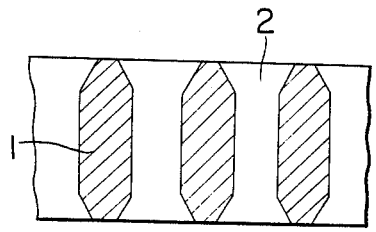 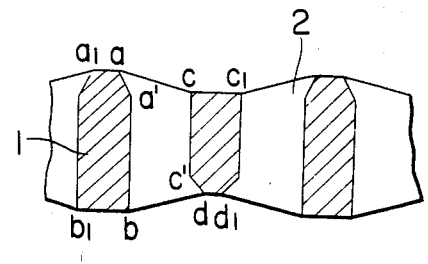
FIG. 3-(vi)    FIG. 3-(vii)
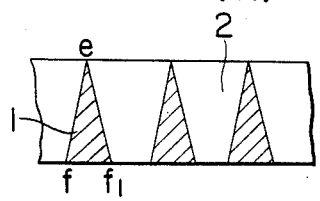 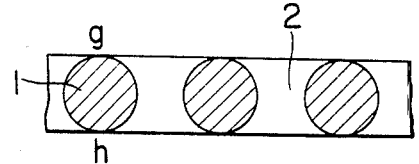

FIG. 7-(i) 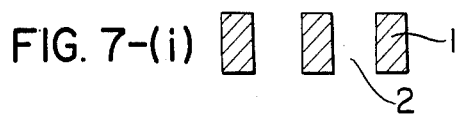
FIG. 7-(ii) 
FIG. 7-(iii) 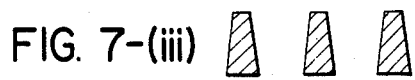   FIG. 7-(x) 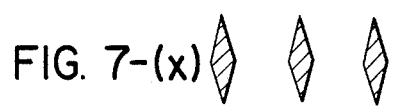
FIG. 7-(iv) 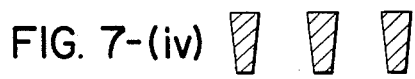
FIG. 7-(xi) 
FIG. 7-(v) 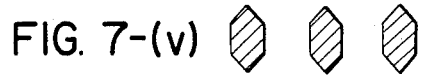
FIG. 7-(vi) 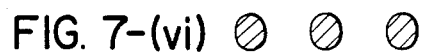
FIG. 7-(xii) 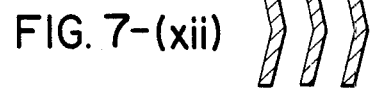
FIG. 7-(vii) 
FIG. 7-(viii) 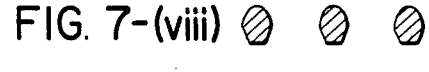  FIG. 7-(xiii) 
FIG. 7-(ix) 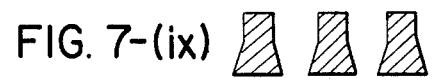

PACKED COLUMN HAVING PRESSURE-ABSORBING MECHANISM

This invention relates to a packed column having a mechanism for reducing a pressure to be applied to packings.

When materials are industrially separated by using a packed column, it is necessary to use a large packed column. However, large packed columns have been disadvantageous in that the pressure loss increases because of, for example, distruction or deformation of packings. In order to solve such a problem, it is known to use, for example, a pressure-absorbing mechanism for supporting packings in the middle of the packed column, as disclosed in British Pat. No. 1,203,439. As said pressure-absorbing mechanism, there have generally been used those having such a structure that the packings are partitioned and supported by a net or the like through which a fluid can pass but the packings cannot. However, such pressure-absorbing mechanisms having a structure through which packings cannot pass have been disadvantageous not only in that the structures of the mechanisms are per se complicated but also in that the structure of the packed column and the packing operation are complicated, because pipe, valves, nozzles and the like are required to be provided in order to pack the packings into each packing section partitioned by said mechanism, or the packed column is required to be designed so that sections can be assembled which packing successively them with packings.

In order to solve these problems as to the packed columns having such a conventional pressure-absorbing mechanism, the present inventors have conducted extensive research, and have consequently developed a pressure-absorbing mechanism which has a simple structure and causes only slight mixing of a moving phase fluid. It has also been found that when this pressure-absorbing mechanism is used packed column having excellent performance characteristics can be obtained.

According to this invention, there is provided a packed column having a pressure-absorbing mechanism, characterized in that (1) the inside diameter [D(cm)] of the column is 10 cm or more, (2) the pressure-absorbing mechanism comprises solid parts and passage spaces formed thereby through which packings can pass, (3) the circumference ratios as defined herein of most of the passage spaces are (10/D) or more and their lengths (cm) in the flow direction are larger than the $-1.5$th power of the circumpference ratio, (4) the passage spaces exist within 1 cm from any position on the upper and lower sides of most of the aforesaid solid parts, and (5) the shielding degree as defined herein of the pressure-absorbing mechanism is 0.01 or more and 0.8 or less.

According to this invention, it is possible to simplify the structure of the packed column, to impart a sufficient supporting ability to the column, and to reduce the disorder of flow of fluid, by allowing the packed column to have the above-mentioned pressure-absorbing mechanism.

According to this invention, it is sufficient that an inlet for charging packings is provided only in the upper part of the packed column, and the structure and piping of the packed column can be made very simple as compared with those of packed columns using a conventional pressure-absorbing mechanism which requires an inlet for each section.

Further, this invention is characterized in that since packings can substantially uniformly be placed in the whole column by supplying the packings to the highest section of the column, this invention, as compared with conventional apparatus, facilitates not only the initial packing of the column but also additional packing, for example, in the case where the height of the packing layer or the like varies in the course of operation and it becomes necessary to additionally supply the packings.

The pressure-absorbing mechanism in the packed column of this invention comprises solid parts subjected to the pressure of a packing layer and passage spaces.

This invention is illustrated below referring to the accompanying drawings. In the accompanying drawings, FIG. 1 is a partially sectioned perspective view of the packed column having a pressure-absorbing mechanism of this invention;

FIG. 2 is a cross-sectional view of the pressure-absorbing mechanism in FIG. 2;

FIG. 3-(i) to FIG. 3-(vii) are partial views vertically sectioned along the III—III line in FIG. 2;

Figure 8:
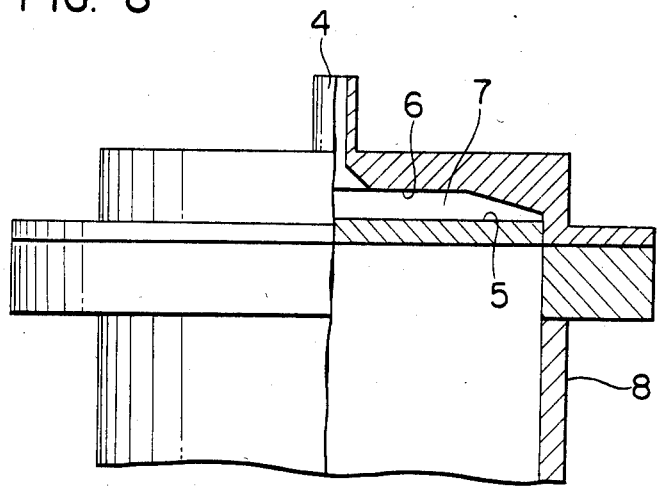
Figure 9:
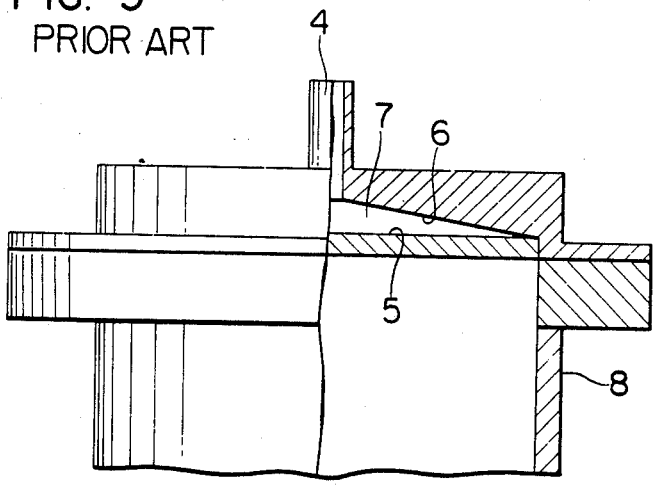
Figure 10:
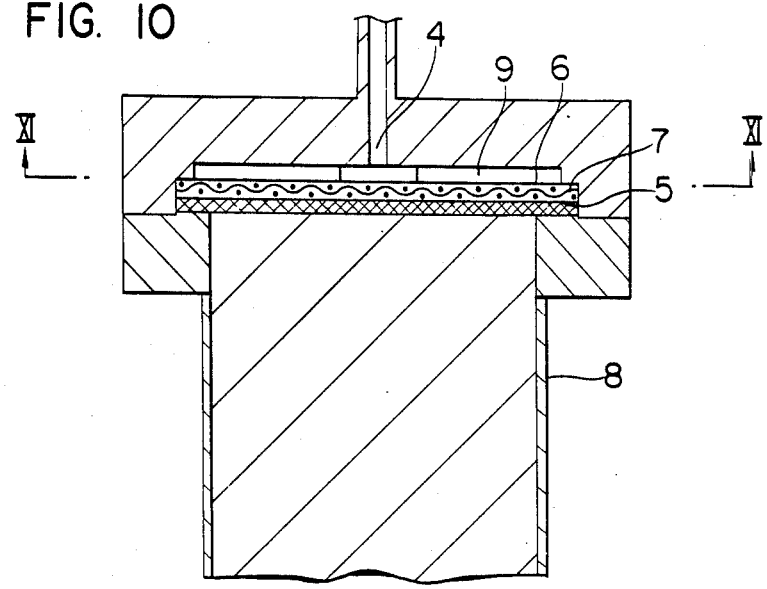
Figure 11:
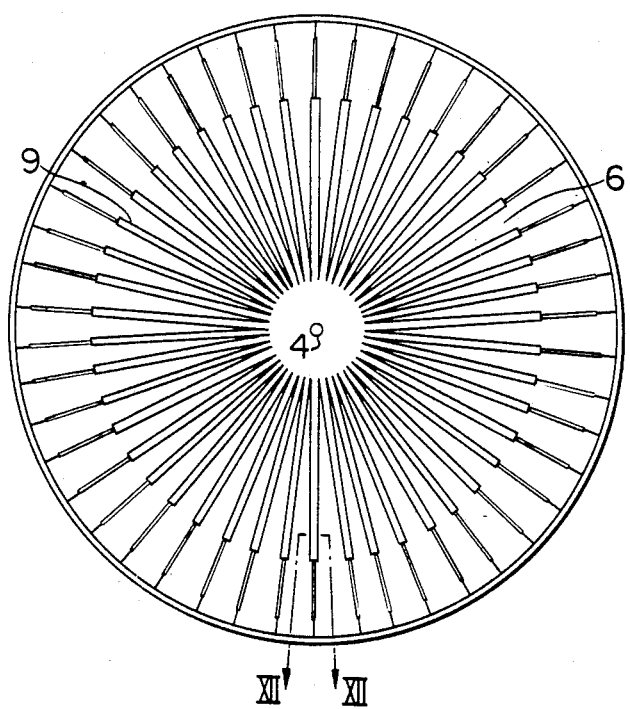
Figure 12:
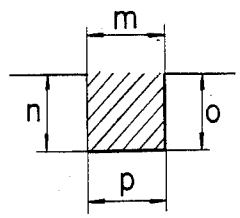
Figure 13:
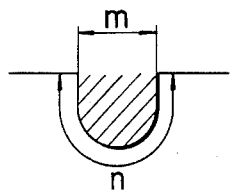
Figure 14:
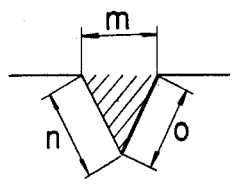
Figure 29:
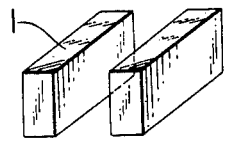
Figure 30:
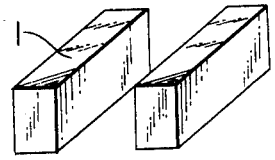

FIG. 7-(i) to FIG. 7-(xiii) are vertically sectioned views of preferable examples of the pressure-absorbing mechanism;

FIG. 8 is a partially cross-sectioned view of an example of the distributor-collector of this invention;

FIG. 9 is a partial crosssectioned view of the prior art distributor-collector which is analogous to FIG. 8;

FIG. 10 is a cross-sectional view of another example of the distributor-collector of this invention;

FIG. 11 is a part of a cross-sectioned view along the XI—XI line in FIG. 10;

FIGS. 12 to 14 are views sectioned along the XII—XII line in FIG. 11;

FIGS. 15 to 21 are perspective views showing the shape and size of the solid parts of the pressure-absorbing mechanism used in Example 1;

FIGS. 22 to 28 are cross-sectional views showing the shape and size of the solid part of the pressure-absorbing mechanism used in Example 2;

FIG. 29 and FIG. 30 are perspective views showing the shape and size of the solid part of the pressure-absorbing mechanism used in Example 4.

As to the reference numerals in the drawings, 1 shows a solid part of a pressure-absorbing mechanism, 2 a passage space of the mechanism, 3 a beam supporting a pressure-absorbing mechanism, 4 an outlet-inlet of a distributor-collector, 5 the A surface of the distributor-collector, 6 the B surface of the distributor-collector, 7 a cavity of the outlet-inlet, 8 the column body, and 9 a groove of the distributor-collector. The unit of the sizes in FIGS. 15 to 30 is mm.

The term "passage spaces" used herein means spaces in the pressure-absorbing mechanism as shown by the reference numeral 2 in FIG. 2 and correspond to the unhatched portions in FIGS. 3(i) to 3(vii). Each of the spaces is defined by the walls of the solid parts surrounding the space, the plane or curved surface having the minimum area contacting the upper ends of the said solid parts and the plane or curved surface having the minimum area contacting the lower ends of the said solid parts. However, when the inside wall of the packed column is a part of the surfaces defining the passage space, the aforesaid planes or curved surfaces are extrapolated perpendicularly to the inside wall of the packed column and the inside wall part between the upper and lower planes or curved surfaces is regarded as a part of the solid parts.

The term "circumference ratio" used herein means the largest value obtained by dividing the length [$l_1$(cm)] of the circumference of the cross-section formed by cutting one of the passage spaces at any position by a plane perpendicular to the center line of the packed column (hereinafter referred to as "the cross-section of column") by the cross-sectional area [$S_1$(cm$^2$)] of the said cross-section. That is to say, when the circumference ratio is taken as $\rho$, $\rho$=[maximum of ($l_1/S_1$)].

The range of the circumference ratio according to this invention is 10/D or more, preferably 0.2 to 10.

The preferable range of the circumference ratio varies depending on the form of the packings. For example, when the packings are in the spherical, powdery, granular or ground form, the most preferable range of the circumference ratio is 1 to 10, and when the packings are a mixture of a filament or a fiber and a spherical, powdery, granular or ground material, the circumference ratio is 0.2 to 2.

When the circumference ratio is small, the pressure-absorbing effect decreases, and when it is large, the mixing of the moving phase fluid occurs, so that the separating ability of the packed column tends to be reduced.

The term "the length in the flow direction of a passage space" [$l_2$(cm)] used herein means the average value of the lengthes in the flow direction of the walls surrounding a passage space. The term "the lengths in the flow direction of the walls" means the distances between the upper and lower sides of the wall of a solid part measured in such a direction that the minimum length is given when a segment of a line which is parallel to the center line of the packed column is projected on the wall of the solid part. Referring to FIG. 3-(v), a-a'-b, c-c'-d and the like correspond said lengths. The average value calculated by integrating these lengths throughout the whole circumference of the passage space and dividing the integrated value of lengths by the length of the circumference ($l_1$) defining $\rho$ is called "the length in the flow direction of a passage space". In this invention, $l_2$ is larger than the $-1.5$th power of the circumference ratio $\rho$. Further, $l_2$ is more preferably in a range of from 0.5 cm to 50 cm.

When $l_2$ is small, the strength of the pressure-absorbing mechanism becomes insufficient, and moreover its pressure-absorbing effect is decreased. When $l_2$ exceeds 50 cm, the separating ability tends to be lowered.

The term "upper and lower sides of a solid part" used herein means the end surfaces of the solid parts defining each passage space corresponding to the top and the bottom in respect to the flow direction of fluid in the packed column. When FIG. 3-(v) is referred to as an example, the surfaces a-$a_1$, b-$b_1$, c-$c_1$ and d-$d_1$ correspond to the end surfaces. Even in the extreme case where the areas of a-$a_1$, b-$b_1$, c-$c_1$ and d-$d_1$ are zero, they are called "end surfaces". For example, positions corresponding to e, g and h in FIG. 3-(vi) and FIG. 3-(vii) are also called "end surfaces".

In this invention, as to the distribution of the passage spaces, it is necessary that the passage spaces be present within 1 cm from any position on the upper and lower sides of the solid part. Owing to such distribution of the passage spaces, the influence of the solid parts on the moving phase fluid can be diminished.

The term "shielding degree" used herein means the largest of the values obtained when the packed column with the pressure-absorbing mechanism is cut by a plane perpendiculary to the center line of the column, the sum total of the cross-sectional areas of the solid parts inside the column obtained is divided by the cross-sectional area of the inside of the column obtained, and the same procedure is repeated by shifting the cutting plane continuously.

The shielding degree must be 0.01 to 0.8. When it is less than 0.01, the pressure-absorbing effect is insufficient, and when it exceeds 0.8, the influence on the moving phase fluid is increased, and the separating ability is reduced.

The preferable range of the shielding degree is varied depending upon the average height of the pressure-absorbing mechanism. When the average height is 0.1 to 1 cm, the shielding degree is preferably 0.7 to 0.3; when it is 1 to 5 cm, the shielding degree is preferably 0.5 to 0.1; and when it is 5 to 50 cm, the shielding degree is preferably 0.3 to 0.03. The term "the average height of the pressure-absorbing mechanism" used above means a value obtained by calculating the average value of the lengths of the solid parts of the pressure-absorbing mechanism inside the column in the longitudinal direction of the column.

Figure 4:
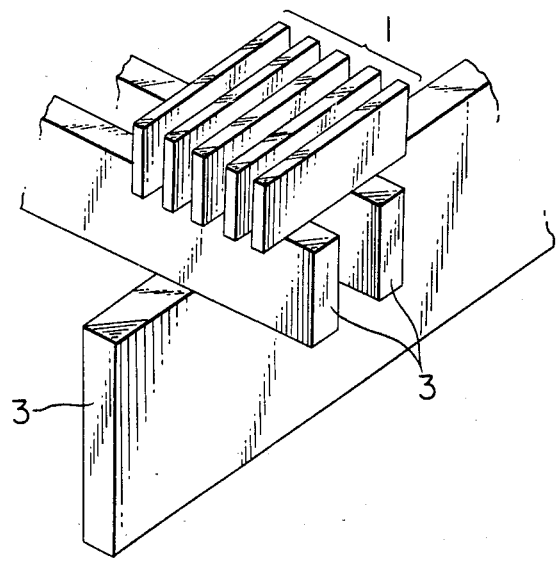
FIG. 4 is a partial perspective view showing one example of beams supporting the pressure-absorbing mechanism.

The pressure-absorbing mechanism of this invention can be used as it is when it has a sufficient strength for supporting the pressure, for example, when the pressure applied to the pressure-absorbing mechanism is low or when the inside diameter of the packed column is small. However, when the pressure-absorbing mechanism has no sufficient strength, it is necessary to provide pillars, beams or the like as shown in FIG. 4 in order to support the pressure-absorbing mechanism of this invention. These pillars, beams and the like preferably have a structure which causes only slight stagnation or mixing of the fluid. Particularly in the case of pillars, the widthes of the upper and lower sides thereof in the flow direction are preferably adjusted to 5 cm or less. When such pillars are provided, they are preferably arranged, for example, in parallel crosses on different levels as shown in FIG. 4.

Figure 5:
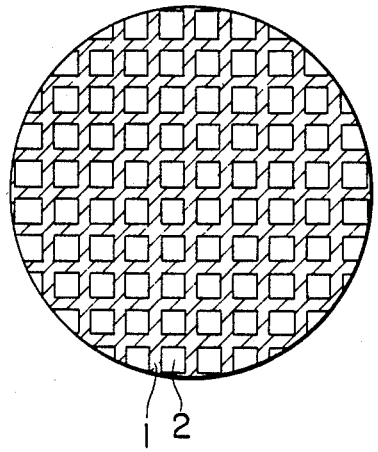
FIG. 5 is a cross-sectional view of a latticed pressure-absorbing mechanism which is a modification of FIG. 2.
Figure 6:
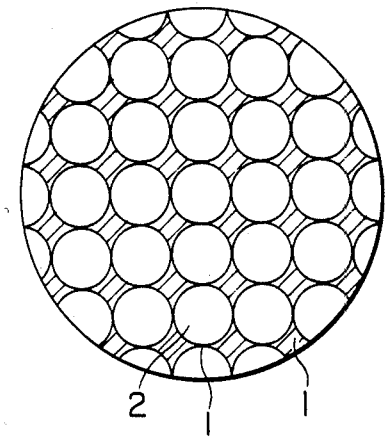
FIG. 6 is a cross-sectional view of a porous-plate-like or cylindrical pressure-absorbing mechanism which is another modification of FIG. 2.

As to the form of the pressure-absorbing mechanism according to this invention, various forms may be used such as lattice form, porous-plate form, cylindrical form and the like as shown in FIGS. 5 and 6 in addition to the drainboard form shown in FIG. 2.

Details of preferable examples of the solid part and the passage space are shown in FIG. 7-(i) to FIG. 7-(xiii) as a section along the III—III line in FIG. 2.

As exemplified in FIGS. 7-(ii), 7-(iii), 7-(v), 7-(vi), 7-(vii), 7-(viii), 7-(ix), 7-(x), 7-(xii) and 7-(xiii), a structure having a positive slope in relation to the flow direction is more preferable. The term "a positive slope in relation to the flow direction" used above means a plane provided in such direction that the plane interrupts the flow of the fluid in the packed column.

The passage space in this invention is preferably in the following form in order to reduce the disorder of flow of the fluid: That is to say, when the passage space is cut by a plane parallel to the longitudinal direction of the packed column, the width of the resulting section is constant, monotonously decreases, shows a combination thereof, in the direction from one of the upper and lower sides to the other; or the width decreases and then immediately increases; or decreases and thereafter becomes constant and then increases, in the same direction as above. Several concrete examples of such preferable forms of the section of the passage space are as shown in FIGS. 7-(i) to 7-(xiii).

Although the pressure-absorbing mechanism of this invention is most preferably provided throughout the column cross-section, a sufficient effect is obtained if the cross-sectional area of the passage spaces having the characteristics of this invention is 50% or more of the total cross-sectional area of the passage spaces in the column cross-section referred to in definition of the shielding degree.

Further, a sufficient effect is obtained when in the upper or lower side of the solid part, the zone in which no passage space exists within 1 cm is less than 10% of the total area of the upper or lower sides.

The packed column according to this invention is effective particularly when the inside diameter of the column is large. That is to say, the packed column of this invention has a significant effect when it has an inside diameter of 10 cm or more, though the inside diameter is preferably at least 30 cm, more preferably at least 60 cm.

The packed column of this invention is improved in performance characteristics by installing, as described above, a distributor-collector on the input side and/or the output side of the packed column.

The distributor-collector is a means which is placed at the inlet or the outlet and serves to distribute a fluid uniformly and rapidly in the direction of the radius of the packed column while suppressing the disorder of the fluid flow as much as possible before the charged fluid is brought into contact with the packings, and to rapidly collect the fluid that the contact with the packings has been completed, while suppressing the disorder of the fluid flow as much as possible.

The distributor-collector installed in the packed column of this invention has a cavity in its inside, and the average distance [$l_3$(cm)] between the following two surfaces A and B forming the cavity is defined as $l_3 = kD^{2/3}$ in which $0.004 \leq k \leq 0.04$:

Surface A: an end surface of a segregating material or a porous plate for supporting the segregating material, through which the fluid can pass but the packings cannot, said surface being nearer to the outlet or inlet than the other end surface.

Surface B: a surface of the part to which the outlet or inlet is connected, said surface facing the A surface.

In the above equation, $l_3$ is a value obtained by dividing the volume of the cavity formed between the surfaces A and B by the cavity area.

The cavity area means the maximum of the areas of the cavity projected on a plane parallel to the column cross-section. When the maximum exceeds the cross-sectional area of the inside of the column, the cross-sectional area of the inside of the column is taken as the cavity area.

The volume of the cavity does not include the volume of the inside of the outlet-inlet, and the outlet-inlet is partitioned from the cavity by the plane defined by connecting the points at which the inclination of the B surface 6 in FIG. 8 to the column cross-section exceeds 30°.

In the present distributor-collector, when k is in the range of $0.004 \leq k \leq 0.04$, the disorder of the flow of fluid caused when the fluid passes through the distributor-collector can be reduced. When the k value is more than 0.04, the volume of the cavity of the distributor-collector increases, the disorder of the flow of fluid caused when the fluid passes through the cavity becomes serious, and the time lag in the flow of fluid in relation to the position of the column cross-section tends to become great. Therefore, such k values are not desirable. When the k value is less than 0.004, the flow of the fluid in the distributor-collector becomes ununiform, or the flow condition of the fluid flowing through the cavity is greatly altered by a slight deformation of the A and B surfaces forming the cavity, so that stable performance is not realized. Therefore, such k values are neither desirable.

Particularly in a packed column aiming at separating substances by chromatogrpahy, the disorder of the flow of fluid influences the separation efficiency greatly, and therefore, the k value is preferably adjusted to a range of $0.005 \leq k \leq 0.03$.

The cavity may be formed so as to be a substantially complete space by reinforcing the segregating material constituting the A surface by inserting partially spacers or the like between it and the B surface, for the purpose of forming a rigid structure, or may be formed by inserting spacers having many voids between the A and B surfaces throughout the whole surface.

As the spacer having many voids, there may be used a sheet formed by regularly or irregularly aligning filaments made of a polymer such as plastics or the like or an inorganic material such as a metal, ceramics or the like, said filaments having a mean cross-sectional area of 0.01 mm$^2$ or more when cutting the filaments perpendicularly to the longitudinal direction, a sheet formed by weaving said filaments, said sheet having a void percentage of at least 60%, preferably at least 70%. Said filaments may be either finely cut or infinitely continuous. The void percentage is calculated as [1-v/(S$_2$xt)]×100 (%) in which t is the thickness (cm) measured under a load of 100 g/cm$^2$ applied to between two plates in between which said sheet is sandwiched, S$_2$ is the area of said sheet (cm$^2$) and v is the excluded volume (cm$^3$) of said sheet. The term "excluded volume" means the volume of water increased when said sheet is immersed in water.

Although the cavity is formed by inserting the spacer having many voids between the A and B surfaces, the spacer and the A surface may be unified. That is to say, for example, the spacer and the A surface may be unified with an adhesive; the surface of the spacer may be densely woven by a spacial weaving method such as twilling or the like to allow the surface to serve as the A surface (a segregating material), and the surface of a sheet of a thermoplastic material may be made dense by means of a hot calender or the like to allow the surface to serve as the A surface (a segregating material).

As the segregating material, there may be used materials through which fluid can pass but packings cannot, such as nets, cloth, porous sheets, porous plates, nonwoven fabrics, filter paper, fine lattices and the like.

It is more preferable that the B surface or the distance between the A and B surfaces has the following characteristics.

[1] The A and B surfaces form the structure that the distance between them is constant in most directions from the outlet-inlet to the circumference within a distance of 20% or more and 80% or less of the distance between the outlet-inlet and the circumference, and in the other part closer to the circumference than the said part where the distance between the surfaces is constant, the distance between the surfaces becomes small as the part approaches to the circumference.

The term "most directions" means such an extent that the distributor-collector of this invention can sufficiently exhibit its effect, and it is sufficient that the sum total of the angles of parts where the distributor-collector has the form of this invention is 300° or more around the outlet-inlet as a center.

[2] The B surface has grooves arranged radially from the opeining of the outlet-inlet.

The cross-sectional view of one example of the distributor-collector of [1] is shown in FIG. 8. Reference numeral 4 shows an outlet-inlet, 5 the A surface, 6 the B surface, 7 a cavity, and 8 the packed column body.

Since the distance between the A and B surfaces decreases in the vicinity of the circumference in the cavity where the amount of the flowing fluid is smaller than in the vicinity of the outlet-inlet, the flow rate of the fluid is not decreased, so that it becomes possible to reduce the time lag in the flow of the fluid in the vicinity of the circumference.

When the distance between the A and B surfaces in the vicinity of the center is constant, the distributor-collector of this invention enables the narrowing of the parts that the distance between the A and B surfaces is extremely small in the vicinity of the circumference, as compared with the case where as shown in FIG. 9, the B surface has only one slope and there is such a taper that the distance between the A and B surfaces increases with a decrease of the distance from the center, so that the part that the fluid flows with difficulty can be narrowed and a smooth flowing can be realized.

Further, it is desirable that in said distributor-collector, the distance between the A and B surfaces in the circumference is the minimum in said cavity and is 0.5 mm or more. When such a structure is employed, there is no part where the distance of the cavity is zero in the circumference, and therefore the flow of the fluid in the circumference becomes smoother, so that it becomes possible to reduce the disorder of the flow of fluid.

FIG. 10 shows a cross-sectional view of the distributor-collector of [2], and FIG. 11 shows a cross-sectional view along the XI—XI line in FIG. 10. In FIGS. 10 and 11, reference numeral 4 shows an outlet-inlet, 5 the A surface, 6 the B surface, 7 the cavity (in this case, a spacer having voids is used to form the cavity), 8 the packed column body, and 9 grooves.

In this invention, a fluid charged through the inlet 4 flows rapidly through the grooves 9 to the circumference, overspreads from the grooves through the cavity 7, and flows into a packing layer. The fluid having passes through the packing layer flows, via the A surface 5, through the cavity 7 into the grooves 9, and is rapidly discharged from the column through the grooves. Since the fluid is thus rapidly and wholly distributed or collected, the residence time of the fluid in the distributor-collector is short, and moreover, the fluid flows rapidly from the opening of the outlet to any point on the segregating surface.

The grooves in said distributor-collector are formed radially around the outlet-inlet in the B surface as a center. That is to say, the grooves are formed so that they gradually go away from the outlet-inlet. The grooves are not always linear and there may be branch grooves branched from the main grooves formed radially. When the cross-sectional area of the groove in the direction perpendicular to the longitudinal direction of the groove is taken as $S_3(mm^2)$ and the average distance of the cavity is taken as $l_3$, $S_3$ is preferably in the range of $100 \, l_3^2 < S_3^2 < 100(10l_3+1)^2$. When $S_3$ is in the range shown by the above formula, the residence time is particularly short, the inner pressure loss in the grooves decreases, the effects of the grooves are marked, and the separating ability of the whole packed column is greatly improved.

The grooves are preferably distributed throughout the B surface as densely and uniformly as possible.

The number of the grooves is not critical, but when the grooves are arranged so that any of them is certainly situated within a distance of $316\sqrt{l_3}$ (mm) from any point on the B surface, the grooves are wholly and uniformly distributed; therefore it is preferably. From the viewpoint of the residence time of the liquid in the grooves and back mixing, it is preferred that the total area of the grooves on the B surface does not exceed 40% of the area of the B surface. Although the form of the groove is also not critical, the cross-section at right angles to the longitudinal direction of the groove may be, for example, triangular, square or circular as shown in FIGS. 12 to 14. In particular, it is preferred that there is a relationship of $\sqrt{S_3} \geq 0.2l_4$ between the cross-sectional area $S_3$ of the groove shown by hatching in FIGS. 12 to 14 and the circumference $l_4$ (mm) of the section of the groove, because in this case, only a small loss due to pressure is caused and good performance characteristics can be obtianed. In this case, $l_4$ is the sum of the circumference of the groove and the width of the groove shown by m in FIGS. 12 to 14. That is, in FIG. 12, $l_4 = m+n+o+p$; in FIG. 13, $l_4 = m+n$, and in FIG. 14, $l_4 = m+n+o$.

The volume of the space in the groove is excluded from that of the cavity of the distributor-collector and is not counted in the calculation of the average distance.

Although the packed column of this invention can also be used as a packed column in which a reaction is conducted with a catalyst supported on packings, or as a packed column for increasing the reaction surface area by providing packings, the characteristics of the present packed column can further be exhibited when used as a packed column for separating two or more substances by chromatography. In particular, excellent effects can be obtained by using the present packed column for separating, by chromatography, substances which have a small separation coefficient, for example, rare earth elements, isotopes and the like.

The packings used in the packed column of this invention may be in various forms such as spherical form, powdery form, glanular form, ground form, fibrous form and the like. Examples of the packings include various materials in the gel state such as silica gel, activated alumina, metal hydroxides, polystyrene gels and the like; various fibrous materials such as cellulosic ion-exchange fibers; active carbon; zeolite; molecular sieves; ion-exchange resins; and materials obtained by supporting on the above-mentioned materials various catalysts such as metals, metal oxides and the like or various organic solutions; and packings obtained by mixing the above-mentioned materials with various short fibers.

The packed column of this invention parmits chromatography at a high flow rate with almost no increase in the disorder of flow of the moving phase fluid, and hence has a very high industrial value.

EXAMPLE 1

Figure 1:
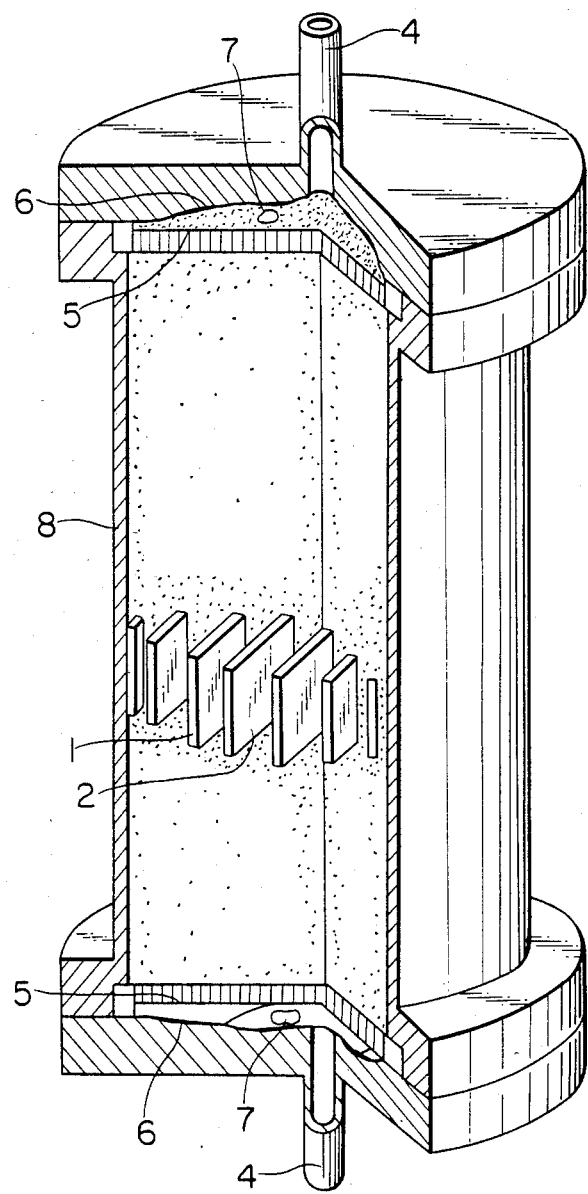

A pressure-absorbing mechanism made of SUS shown in any of FIGS. 15 to 21 was installed at the middle, namely a height of 0.9 m from the bottom, of a jacketed column having an inside diameter of 30 cm and a height of 1.8 m, as shown in FIG. 1. Further, distributor-collectors as shown in FIG. 8 were installed on the input and output sides of the packed column. In these distributor-collectors, the radius of the cavity was 15 cm, the radius of a part where the A and B surfaces were parallel to each other was 7.5 cm, the distance between the A and B surfaces in said part was 2.5 mm, the distance in the circumference of the cavity was 0.5 mm, and k=0.016. As the A surface, a Teflon nonwoven fabric reinforced with a porous plate was used. Into the packed column was charged from the upper part a cation exchange resin composed of sulfonation product of styrene-divinylbenzene copolymer which has been classified using 100 to 200 mesh. The crosslinking degree of the cation-exchange resin was 20.

Subsequently, 900 liters of a surfuric acid solution having a concentration of 0.5 mol/liter was supplied from the upper part of the packed column to convert the cation-exchange resin into its hydrogen ion form. The packed column was maintened at 95° C., and a solution containing 7.5 mmols/liter of neodymium, 7.5 mmols/liter of praseodymium and 15 m mols/liter of EDTA which had been adjusted to pH 3 was supplied from the upper part of the packed column while heating the same at 95° C. This supply was continued until the width of adsorption band of the rare earth element ions reached 120 cm.

Thereafter, an EDTA solution having a concentration of 15 mmols/liter was supplied to develope and shift the adsorption band of the rare earth element ions. The supply speed of the solution during this procedure was as shown in Table 1 so that the pressure loss was near the pressure resistance of the packed column of 15 kg/cm². A part of the solution effluent from the lower part of the packed column was continuously collected, and divided into fractions of 15 ml, and the amounts of neodymium and praseodymium in the fractions were determined by fluorescent X-ray analysis.

The amount of praseodymium obtained per unit time (Pr yield) was calculated by dividing the yield of praseodimium having a purity of 99.9% or higher by the time required for the development. The results were shown in Table 1.

TABLE 1

Figure 15:
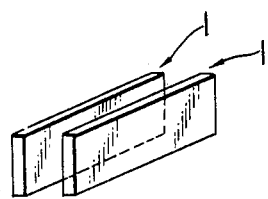
Figure 16:
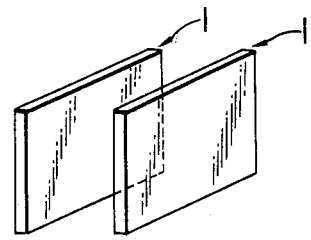
Figure 17:
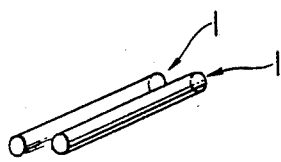
Figure 18:
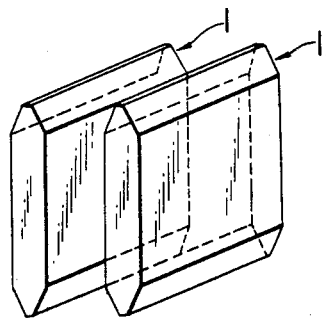
Figure 19:
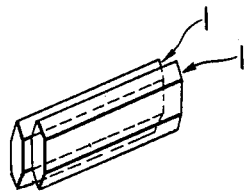
Figure 20:
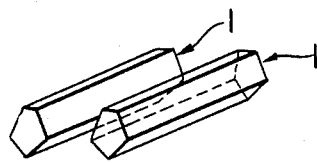
Figure 21:
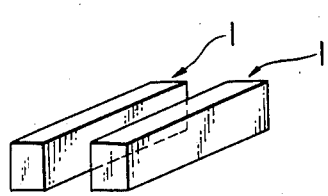

| Run No. | Form of constituent of pressure-absorbing mechanism | Speed of developing solution (liter/min) | Pr yield (mol/hr) |
| --- | --- | --- | --- |
| 1 | FIG. 15 | 10.9 | 1.18 |
| 2 | FIG. 16 | 9.5 | 1.07 |
| 3 | FIG. 17 | 10.0 | 1.01 |
| 4 | FIG. 18 | 8.8 | 0.96 |
| 5 | FIG. 19 | 14.5 | 1.43 |
| 6 | FIG. 20 | 10.2 | 1.04 |
| 7 | FIG. 21 | 9.8 | 1.13 |

COMPARATIVE EXAMPLE 1

The same cation-exchange resin as in Example 1 was packed into the same column as in Example 1, except that the pressure-absorbing mechanism was not installed therein, and praseodymium was separated by the same procedure as in Example 1. The speed of a developing solution was 5.8 liters/min and the Pr yield was 0.74 mol/hr.

EXAMPLE 2

Figure 25:
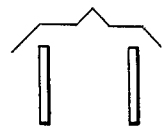
Figure 26:
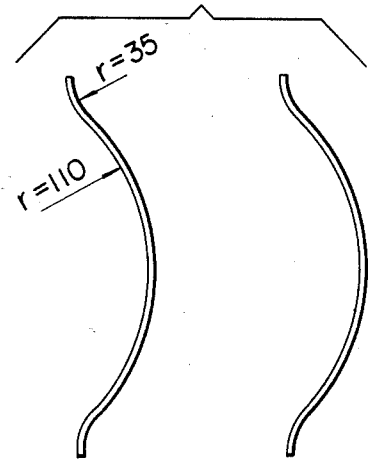
Figure 27:
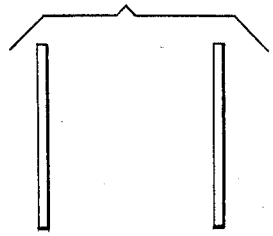
Figure 28:
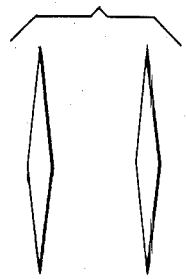

A pressure-absorbing mechanism having a section shown in any of FIGS. 22 to 26 was installed in the form of a drainboard as shown in FIGS. 1 and 2 at the middle of a column having an inside diameter of 700 mm⌀ and a height of 2 m, or a pressure-absorbing mechanism having a section as shown in FIG. 27 or FIG. 28 was installed at said middle in the form of a lattice as shown in FIG. 5. Further, distributor-collectors having grooves as shown in FIG. 10 or FIG. 11 were installed on the input and output sides of the packed column. The grooves had a linear form and were arranged radially at a pitch of 7.5°, and the number of the grooves was 48. The grooves had a width of 6 mm and a depth of 4 mm within a distance of 26 cm from the outlet-inlet and had a width of 4 mm and a depth of 4 mm at a distance therefrom of 26 cm to 34 cm. As the A surface, a Teflon cloth was used, and a wire gauze of 20 mesh was inserted in order to form spaces. In this case, the radius of the cavity was 35 cm, the distance in the cavity was 1 mm, and k=0.006. The following investigation was made for the packed column in each of the cases described above.

The above-mentioned column was packed with packings prepared by mixing a short fiber obtained by cutting carbon fibers having a diameter of 7 μm into 1.0 mm in a proportion of 30% by weight with an anion-exchange resin of vinylpyridine-divinylbenzene copolymer having a crosslinking degree of 15% and a particle diameter of 100 to 200 mesh. Subsequently, a 1 N hydrochloric acid solution was passed through the packed column to condition the packings, after which 100 ml of a sodium chloride solution having a concentration of 2 mols/liter was nomentarily poured into the column through a liquid-supplying inlet installed just before the column inlet while continuing the passing of a 1 N hydrochloric acid solution at a rate of 38.2 liters/min. The solution effluent from the column outlet was collected, and divided into fractions of 1 liter, and the sodium concentration in each of the fractions was measured by means of an atomic absorption analyzer.

On the basis of the values thus measured, the amount of the effluent solution was plotted on the abscissa and the sodium concentration was plotted on the ordinate whereby a pulse wave was obtained. The pulse width at a height of a half of the peak height (half-width) of the pulse was measured, and used as an index of the disorder of flow of the moving phase passing through the packing layer. The maximum flow rate was measured at a pressure loss of 20 kg/cm² in the case where each pressure-absorbing mechanism was installed.

The results are shown in Table 2.

TABLE 2

Figure 22:
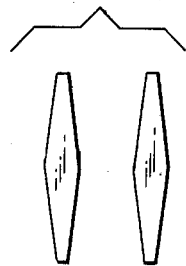
Figure 23:
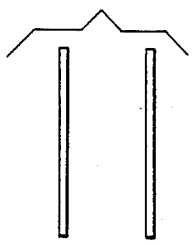
Figure 24:
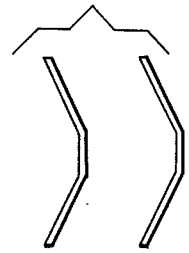

| Run No. | Form of constituent of pressure-absorbing mechanism | Half-width (liter) | Maximum flow rate (liter/min) |
| --- | --- | --- | --- |
| 1 | FIG. 22 | 35.8 | 265 |
| 2 | FIG. 23 | 36.1 | 308 |
| 3 | FIG. 24 | 35.2 | 242 |
| 4 | FIG. 25 | 35.2 | 223 |
| 5 | FIG. 26 | 35.4 | 219 |
| 6 | FIG. 27 | 35.3 | 285 |

TABLE 2-continued

| Run No. | Form of constituent of pressure-absorbing mechanism | Half-width (liter) | Maximum flow rate (liter/min) |
|---|---|---|---|
| 7 | FIG. 28 | 35.1 | 300 |

COMPARATIVE EXAMPLE 2

The same ion-exchange resin and the same short fiber as in Example 2 were packed into the same column as in Example 2 except that the pressure-absorbing mechanism was not installed therein. Evaluation was carried out by the same method as in Example 2 to find that the half-width of the pulse was 35.2 l and that the maximum flow rate was 184 (liters/min).

EXAMPLE 3

The same procedure as in Example 2 was repeated, except that the dimensions for a pressure-absorving mechanism having a section as shown in FIG. 19 were widely varied as shown in Table 3.

TABLE 3

| Run No. | Circumference ratio (cm$^{-1}$) | Length in flow direction (cm) | Shielding degree | Half-width (liter) | Maximum flow rate (liter/min) |
|---|---|---|---|---|---|
| 1 | 0.12–0.13 | 25 | 0.05 | 37.0 | 196 |
| 2 | 0.4–0.5 | 2.5 | 0.3 | 36.2 | 224 |
| 3 | 0.4–0.5 | 10 | 0.3 | 35.4 | 301 |
| 4 | 0.8–1.2 | 5 | 0.3 | 34.9 | 285 |
| 5 | 2–3 | 3 | 0.5 | 35.8 | 265 |
| 6 | 8–12 | 1 | 0.7 | 36.2 | 241 |
| 7 | 8–12 | 1 | 0.85 | 37.3 | 206 |

In the case of Run Nos. 1, 2 and 7, the circumference ratio, the length in the flow direction and the shielding degree were outside the respective ranges of this invention, and the half-width increased, while the maximum rate decreased.

EXAMPLE 4

The performance characteristics of the same packed column as in Example 1 was evaluated, except that a pressure-absorbing mechanism as shown in FIG. 29 or FIG. 30 was installed therein, to obtain the results shown in Table 4.

TABLE 4

| Run No. | Form of pressure-absorbing mechanism | Speed of developing solution (liter/min) | Pr yield (mol/hr) |
|---|---|---|---|
| 1 | FIG. 29 | 11.0 | 0.94 |
| 2 | FIG. 30 | 13.3 | 0.84 |

In the case of Run No. 2, there was used a pressure-absorbing mechanism in which no passage space exists within 1 cm from any position on the upper and lower sides of the solid part, and the Pr yield decreased.

EXAMPLE 5

Zeolite (60 to 100 mesh) was packed into the same column as in Example 2, except that a pressure-absorbing mechanism as shown in FIG. 27 was employed therein.

The column packed with the zeolite was maintained at a temperature of 100° C. Toluene was first supplied to the column to condition the zeolite, after which as a material to be separated, a mixture of C$_6$-compounds consisting of 50% by weight of benzene, 32.5% by weight of cyclohexene and 17.5% by weight of cyclohexane was supplied by means of a measuring pump to form an adsorption band of the mixture of C$_6$-compounds. Thereafter, toluene was again supplied to the column at a constant flow rate of 45 liters/min to develop the adsorption band of the mixture of C$_6$-compounds. The eluate from the bottom of the column was collected, and divided into fractions of 1 to 10 liters. Quantitative analysis was carried out for the percentages by weight of benzene, cyclohexene, cyclohexane and toluene in the sample solutions thus collected, by gas chromatography.

A solution rich in cyclohexene and cyclohexane was recovered in the vicinity of the front-end interface of the adsorption band of C$_6$-compounds in relation to the flowing direction of the eluate, and a solution rich in benzene was recovered in the vicinity of the rear-end interface. The weight of benzene contained in the fraction in which the purity of the benzene in relation to the mixture of C$_6$-compounds, which is a measure of separation efficiency, was 99% or higher was 57.1 kg.

EXAMPLE 6

The same separation procedure as in Example 5 was repeated, except that the distance between the A and B surfaces was 0.5 mm. In this case, the weight of benzene contained in the fraction in which the purity of the benzene was 99% or higher was 52.1 kg. The distributor-collector of the packed column used in this case had a k value of 0.003 (the performance of the distributor-collector was inferior).

COMPARATIVE EXAMPLE 3

The same separation procedure as in Example 5 was repeated, except that the pressure-absorbing mechanism was omitted. In this case, the yield of benzene was 39.4 kg.

EXAMPLE 7

Zeolite (60 to 100 mesh) was packed into the same column as in Example 1, except that a pressure-absorbing mechanism as shown in FIG. 19 was used.

The column packed with the zeolite was maintained at a temperature of 100° C. Toluene was first supplied to the column to condition the zeolite, after which as a material to be separated, 42.1 liters of a mixture of C$_6$-compounds consisting of 50% by weight of benzene, 32.5% by weight of cyclohexene and 17.5% by weight of cyclohexane was supplied by means of a measuring pump to form an adsorption band of the mixture of C$_6$-compounds. Thereafter, toluene was again supplied to the column at a constant flow rate of 8.4 liters/min to develop the adsorption band of the mixture of C$_6$-compounds. The eluate from the bottom of the column was collected, divided into fractions of 0.25 to 2.5 liters. The weight percentages of benzene, cyclohexene, cyclohexane and toluene in the sample solutions thus obtained was quantitatively analyzed by gas chromatography.

A solution rich in cyclohexene and cyclohexane was recovered in the vicinity of the front-end interface of the adsorption band of C$_6$-compounds in relation to the flowing direction of the eluate, and a solution rich in benzene was recovered in the vicinity of the rear-end interface. The weight of benzene contained in the fraction in which the purity of the benzene in relation to the mixture of C$_6$-compounds was 99% or higher was 8.31 kg.

EXAMPLE 8

The same separation procedure as in Example 7 was repeated, except that the distances between the A and B surfaces were 6.5 mm in the part where the surfaces were parallel to each other and 0.6 mm in the circumference. In this case, the yield of benzene was 7.84 kg.

The distributor-collector of the packed column used in this case had a k value of 0.041 (the performance of the distributor-collector was inferior).

COMPARATIVE EXAMPLE 4

The same separation procedure as in Example 7 was repeated, except that the pressure-absorbing mechanism was omitted. In this case, the yield of benzene was 6.57 kg.

What is claimed is:

1. A packed column having a pressure-absorbing mechanism which is used as a reaction column or a column for separating or exchanging solutes, wherein (1) the inside diameter [D(cm)] is 10 cm or more, (2) the pressure-absorbing mechanism comprises solid parts and passage spaces defined thereby, through which spaces packings can pass, (3) the circumference ratio as defined herein of most of the passage spaces is (10/D) or more and their lengths in the flow direction are larger than the $-1.5$th power of the circumference ratio and are not more than 16% of the column length, (4) the passage spaces exist within 1 cm from any position on the upper and lower sides of most of the aforesaid solid parts, and (5) the shielding degree as defined herein of the pressure-absorbing mechanism is 0.01 or more and 0.8 or less.

2. A packed column according to claim 1, wherein the shielding degree is 0.7 to 0.3 when the average height of the pressure-absorbing mechanism is 0.1 to 1 cm; 0.5 to 0.1 when the average height is 1 to 5 cm; or 0.3 to 0.03 when the average height is 5 to 50 cm.

3. A packed column according to claim 1, wherein most of the passage spaces of the pressure-absorbing mechanism have the form that the width of a section of the passage space in the longitudinal direction of the packed column is constant and/or continuously decreases from one end to the other.

4. A packed column according to claim 2 or 3, wherein a distributor-collector is installed on the input side and/or the output side, said distributor-collector having a cavity therein, and the average distance k between the following two surfaces A and B defining the cavity is in the range of $0.004 \leq k \leq 0.04$:

Surface A: an end surface of a segregating material or a porous plate for supporting the segregating material through which fluid can pass but packings cannot, said end surface being nearer to the outlet-inlet than the other end surface, Surface B: a surface of the part to which an outlet or inlet is connected, said surface facing the A surface.

5. A packed column according to claim 4, wherein the distance between the A and B surfaces is constant in most directions from the outlet-inlet to the circumference within a distance of 20% or more and 80% or less of the distance between the outlet-inlet and the circumference, and in the other part closer to the circumference than the said part where the distance between the surfaces is constant the distance between the surfaces becomes small as the said other part approaches the circumference.

6. A packed column according to claim 4, which has grooves formed radially from the outlet-inlet on the B surface.

7. A packed column according to claim 1, wherein most of the passage spaces of the pressure-absorbing mechanism have the form that the width of a section of the passage space in the longitudinal direction of the packed column decreases and subsequently increases from one end to the other.

* * * * *